US00PP14090P39

(12) United States Plant Patent
Dwivedi et al.

(10) Patent No.: US PP14,090 P3
(45) Date of Patent: Aug. 26, 2003

(54) PEPPERMINT PLANT NAMED 'PRANJAL'

(75) Inventors: Samresh Dwivedi, Uttar Pradesh (IN); Maneesha Singh, Uttar Pradesh (IN); Ajay Pratap Singh, Uttar Pradesh (IN); Vandana Singh, Uttar Pradesh (IN); Suman Preet Singh Khanuja, Uttar Pradesh (IN); Ali Arif Naqvi, Uttar Pradesh (IN); Sushil Kumar, Uttar Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/785,716

(22) Filed: Feb. 16, 2001

(65) Prior Publication Data

US 2002/0184676 P1 Dec. 5, 2002

(51) Int. Cl.[7] ..... A01H 5/00
(52) U.S. Cl. ..... Plt./259
(58) Field of Search ..... Plt./259

*Primary Examiner*—Bruce R. Campell
*Assistant Examiner*—June Hwu
(74) *Attorney, Agent, or Firm*—Christie, Paraker & Hale, LLP

(57) ABSTRACT

Described as a new Peppermint mutant having a high yield of menthol rich essential oil, deep purplish green foliage, purplish white flowers, a delayed temporary wilting point and tolerance to the pest Bihar hairy caterpillar (*Spilarctia obliqua*).

3 Drawing Sheets

Latin name of genus and species: The present invention relates to a new *Mentha×piperita* plant.

Variety denomination: The new *Mentha×piperita* plant has the varietal denomination 'Pranjal'.

BACKGROUND OF THE INVENTION

In order to overcome a major bottleneck encountered in the cultivation of peppermint (*Mentha×piperita*), which is low oil yielding coupled with susceptibility to *Spilarctia obliqua* (Bihar hairy caterpillar), a planned breeding program was initiated. The commercial cultivation of *Mentha×piperita* is widely spread in tropical and subtropical climates and its oil finds widespread use in flavoring, cosmetics and pharmaceutical industries. As the *Mentha×piperita* is infertile or little fertile in nature, mutagen treatment and induced ploidy is the most appropriate way to create new genetic variability. Screening of the desired altered genotype is the most important step as most of the induced mutations are deleterious and undesirable. Accordingly, in order to develop a peppermint plant capable of yielding high levels of menthol oil and being resistant to Bihar hairy caterpillar, a planned breeding program was undertaken. The program resulted in a genotype CIMAP/MPP-4 having the varietal denomination 'Pranjal'. This plant of the invention represents induced genetic variability followed by selection for improvement in terms of high oil yield, high menthol content and enhanced level of tolerance towards a common pest (Bihar hairy caterpillar i.e. *Spilarctia obliqua*).

SUMMARY OF THE INVENTION

The present invention relates to a genotype of *Mentha×piperita* named 'Pranjal' and belonging to family Lamiaceae. The new variety is a mutant, developed in a breeding program for resistance to the Bihar hairy caterpillar (*Spilarctia obliqua*) with emphasis on essential oil having high menthol content. The *Mentha×piperita* parent cultivars are non-patented. A locally adopted strain (non-patented) was used for the planned induced mutagenesis experiment.

'Pranjal' is propagated vegetatively through suckers and hence can be maintained as a stable genotype. The plant is a perennial, glabrous and aromatic herb widely cultivated for its essential oil which is of commercial and export value. The following description is of plants grown in Uttar Pradesh, India. The plants as described are 80 to 100 days after transplantation of suckers. Color descriptions are in accordance with The Royal Horticultural Society (R.H.S.) Colour Chart.

BRIEF DESCRIPTION OF ILLUSTRATIONS

The accompanying illustrations depict specimen plants of the new variety in color as true as possible in color photographic illustrations of this nature.

Figure 3:
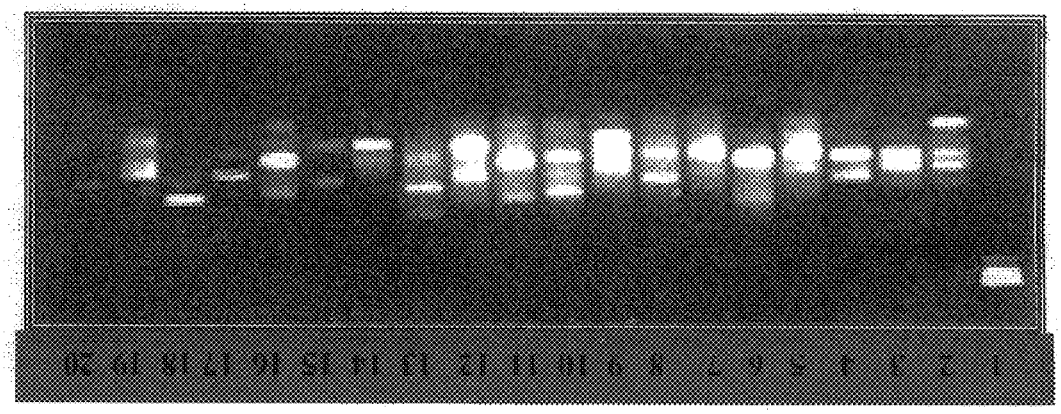

FIG. 3 represents the typical RAPD profile of the new variety. Lane 1: λ HindIII marker. Lanes 2–20: RAPD profiles with the following primers:

| | | |
|---|---|---|
| Lane 2 | AAATCGGAGC | SEQ. ID NO. 1 |
| Lane 3 | TGCGCGATCG | SEQ. ID NO. 4 |
| Lane 4 | CTATCGCCGC | SEQ. ID NO. 7 |
| Lane 5 | CCCTGCAGGC | SEQ. ID NO. 10 |
| Lane 6 | AGGATACGTG | SEQ. ID NO. 13 |
| Lane 7 | TTGTCTCAGG | SEQ. ID NO. 16 |
| Lane 8 | AGCCTGACGC | SEQ. ID NO. 19 |
| Lane 9 | GTCCTACTCG | SEQ. ID NO. 2 |
| Lane 10 | AACGTACGCG | SEQ. ID NO. 5 |
| Lane 11 | CGGGATCCGC | SEQ. ID NO. 8 |
| Lane 12 | CCAAGCTTGC | SEQ. ID NO. 11 |
| Lane 13 | AAGATAGCGG | SEQ. ID NO. 14 |
| Lane 14 | CATCCCGAAC | SEQ. ID NO. 17 |
| Lane 15 | GTCCTTAGCG | SEQ. ID NO. 3 |
| Lane 16 | GCACGCCGGA | SEQ. ID NO. 6 |
| Lane 17 | GCGAATTCCG | SEQ. ID NO. 9 |
| Lane 18 | GTGCAATGAG | SEQ. ID NO. 12 |
| Lane 19 | GGATCTGAAC | SEQ. ID NO. 15 |
| Lane 20 | GGACTCCACG | SEQ. ID NO. 18 |

DESCRIPTION OF THE NEW VARIETY

Figure 1:
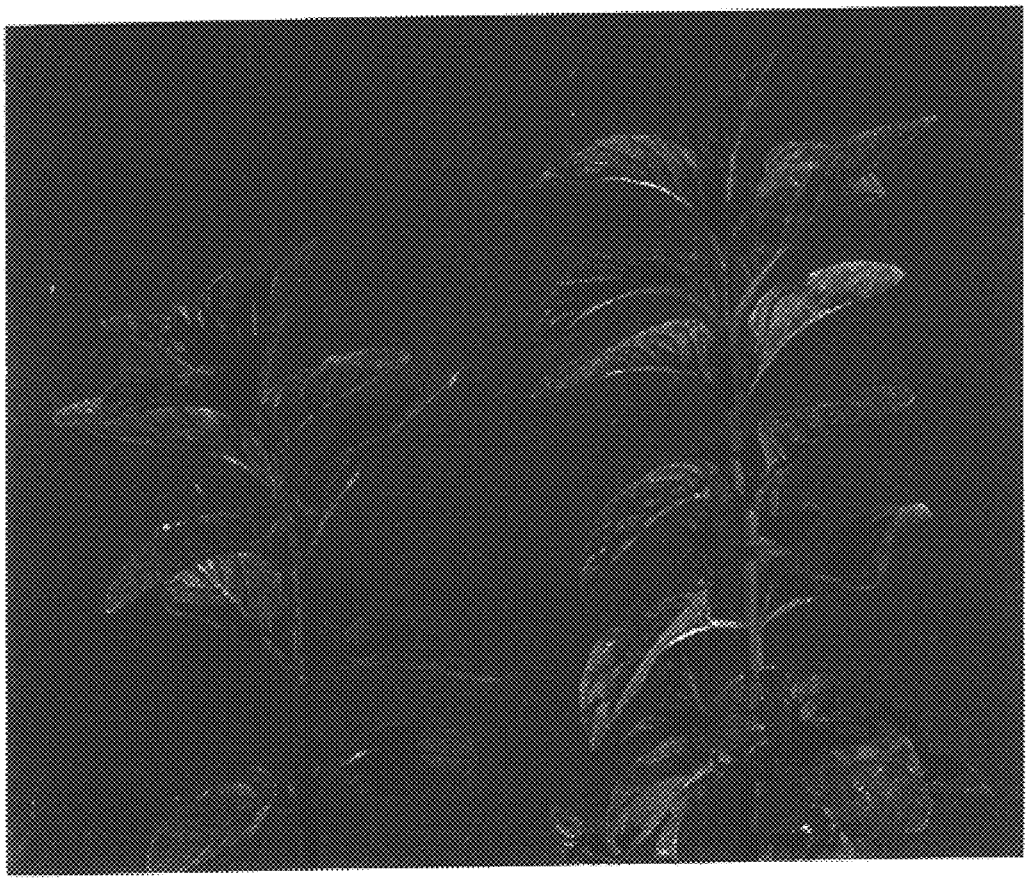
FIG. 1 represents twigs of the new variety.
Figure 2:
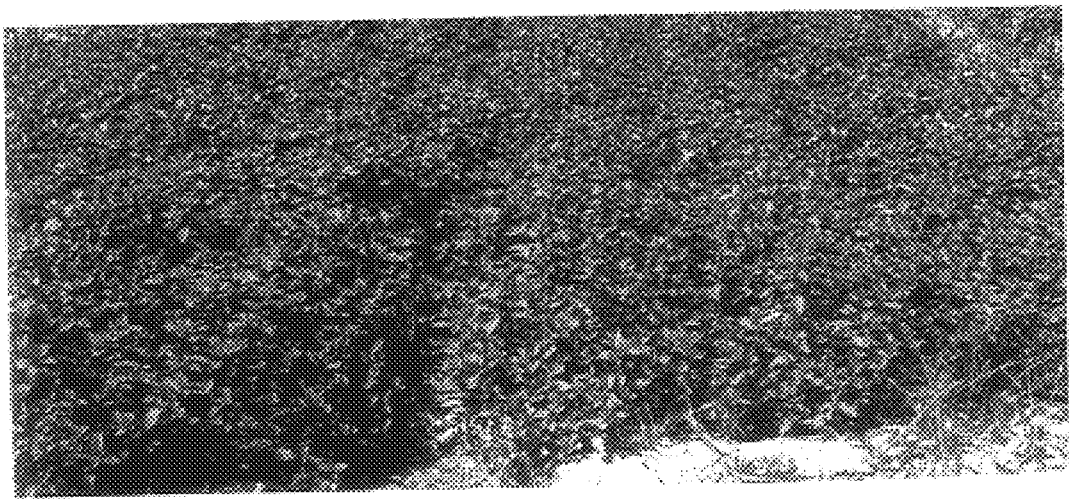
FIG. 2 represents colonies of the new variety.

The girth of the stem of the new variety is between about 1.0 and 2.0 cm girth and typically high pigmentation to serve as a characteristic marker (FIG. 1). The main axis possesses between 15 and 20 nodes with internodes between about 2.5 and 3.0 cm. As seen in FIG. 1, the stem is marked by reddish purple pigmentation; the color generally varies from between 61A to 59B (red purple) on The R.H.S. Colour Chart. As seen in FIGS. 1 and 2, the leaves are found to be of green color, which corresponds to near 146A (green) on The R.H.S. Colour Chart. The leaves and the foliage as such, are marked by reddish purple pigmentation, corresponding to color code near 61A on The R.H.S. Colour Chart. Leaves are also highly pigmented and ovate. Leaf area ranges from between about 5.5 and 6.0 $cm^2$. Fresh herb yield is between 15 and 20 T/ha with oil yield between about 140.0 and 150.0 1/ha of oil. Major oil components detected are menthol, menthone, neo-menthone, menthyl acetate and isomenthone and are in the range of between about 50% and 55%, 12% and 14%, 5% and 8%, 4% and 6% and 3% and 4% respectively. The propagated population of 'Pranjal' is uniform and can be harvested after about 80 to 100 days of sucker transplantation and performs best at about 60 cm inter-row spacing.

'Pranjal' (CIMAP/MPP-4) is thus a new and distinct variety of *Mentha×piperita* having the following combination of characters:

(a) deep purplish green foliage and purplish white flowers;

(b) although seed set occurs, seeds are not viable;

(c) tolerance to Bihar hairy caterpillar (about 30% infestation observed under natural epiphytotic conditions); and (d) stable high oil yields with relatively high content of menthol.

The new variety:

i) has an average of about 40 leaves on its main axis, as compared to 23 found in the control plant 'Kukrail' (non-patented);

ii) has average leaf-stem ratio of about 0.36 which is much higher than the control plant 'Kukrail'. The leaf-stem ratio in the control plant is about 0.26;

iii) exhibits menthol content of about 51.59% in the essential oil as compared to 27.46% in the control plant 'Kukrail'. The oil profile of the new variety shows its constituents as menthone, neo-menthone, menthyl acetate and isomenthone;

iv) provides total oil yield per hectare of about 145.45 as compared to 72.72 1/ha of the control plant 'Kukrail';

v) exhibits greater tolerance (up to about 30%) infestation to the Bihar hairy caterpillar under epiphytotic conditions as compared to the control plant 'Kukrail' (about 70% infestation); and vi) shows temporary willing point (TWP) as compared to the control plant.

The new genotype of the new variety was developed through planned mutational breeding experiments conducted at Central Institute of Medicinal and Aromatic Plants (CIMAP) , Lucknow, India with defined aim to develop superior genotype possessing high oil content with improved oil quality and tolerance to Bihar hairy caterpillar. For this purpose, 2 inch pieces of suckers of locally grown cultivator of *Pantnagar Mentha×piperita* were given 3 treatments (1.5 kR, 3.0 kR, .4.5kR) of –radiation. The irradiated suckers were transplanted in a field with inter-row spacing of 60 cm and 4' distance within a row (FIG. 2) along with control plants. Plants which are not subject to mutagenic treatment are herein referred as 'controls'. The control plant used in the instant invention was 'Kukrail'. Data was recorded for various qualitative and quantitative traits including oil yield and composition. Selection was made on the basis of vigorous plant growth coupled with high oil yield with good quality oil profile. The selected variant was multiplied, tested for homogeneity in the population and further evaluated for performance in M2 through M5 generations.

Considering the variation in morphometric traits, 13 variants were selected from the irradiated plants. These selected variants were multiplied by transplanting the stolons again at 4' distance within a row in order to purify the variant genotypes to homogeneity in the M2 generation and 10 clones with variable morpho-metric characteristics were screened. These clones were grown in replicated trials in M3 and M4 generations in 3 meter rows along with parent and cv. Kukrail following uniform cultural practices to study oil yield and pest tolerance. Out of the 10 clones, 7 performed better than the parent in terms of oil yield. Among the seven, three clones showed better tolerance towards Bihar hairy caterpillar and one among the three was even superior in terms of relatively high content of menthol. This plant bearing number CIMAP/MPP4 in the breeding program was finally christened as 'Pranjal'.

The new variety 'Pranjal' was moderate in height and canopy but was found vigorous as it possessed more number of leaves on its main axis and had greater leaf-stem ratio in comparison to both the parent and cv. Kukrail. The new variety maintained its superior performance over parent and cv. Kukrail in M3 and M4 generations. This plant yielded 145.45 1/ha of oil in comparison to 72.72 1/ha produced by the control plants and was superior in terms of menthol content (51.59% in comparison to 27.46% in control plants).

| | 'PRANJAL' | | |
|---|---|---|---|
| TRAIT | 1998 | 1999 | 2000 |
| Plant Height (cm) | 48 | 48 | 46 |
| Canopy (cm) | 41 | 42 | 43 |
| Stem Girth (cm) | 1.6 | 1.5 | 1.6 |
| Nodes/main axis | 19 | 18 | 20 |
| Average Internode length (cm) | 2.9 | 2.8 | 2.8 |
| Number of main branches | 36 | 36 | 36 |
| Leaf stem ratio | 0.34 | 0.36 | 0.39 |
| Leaves on main axis | 40 | 40 | 40 |
| Leaf area ($cm^2$) | 5.9 | 5.8 | 5.8 |
| Herb Yield (T/ha) | 19 | 18.2 | 18 |
| Oil Content (% V/W) | 0.8 | 0.8 | 0.7 |
| Menthol (% V/V) | 52 | 51.6 | 52 |
| Menthone | 15.7 | 13.6 | 12.2 |
| Neo-menthone | 6.15 | 6.16 | 6.64 |
| Menthyl acetate | 5.61 | 5.44 | 4.63 |
| Iso-menthone | 3.74 | 4.02 | 4.02 |
| Total oil yield (1 ha) | 141.9 | 144.39 | 144.4 |

Comparison variety:

| TRAIT | 'Kukrail' 1998 | 1999 | 2000 |
|---|---|---|---|
| Plant Height (cm) | 52 | 52 | 51 |
| Canopy (cm) | 52 | 52 | 54 |
| Stem Girth (cm) | 1.9 | 1.7 | 1.7 |
| Nodes/main axis | 17 | 18 | 17 |
| Average Internode length (cm) | 2.5 | 2.6 | 2.5 |
| Number of main branches | 34 | 37 | 37 |
| Leaf stem ratio | 0.22 | 0.26 | 0.26 |
| Leaves on main axis | 25 | 23 | 22 |
| Leaf area ($cm^2$) | 5.6 | 5.8 | 5.6 |
| Herb Yield (T/ha) | 18 | 18.2 | 19 |
| Oil Content (% V/W) | 0.5 | 0.45 | 0.47 |
| Menthol (% V/V) | 27.8 | 27.5 | 28.3 |
| Menthone | 22.7 | 23.9 | 22.8 |
| Neo-menthone | 3.4 | 3.26 | 3.46 |
| Menthyl acetate | 2.59 | 2.52 | 2.74 |
| Iso-menthone | 5.12 | 4.48 | 4.58 |
| Total oil yield (1 ha) | 90 | 72.72 | 89.3 |

Comparison of varieties 'Pranjal' versus 'Kukrail' using the following definitions:

| TRAIT | SEM | CD (1%) | CD (3%) |
|---|---|---|---|
| Plant Height (cm) | 1.67 | 7.46 | 5.25 |
| Canopy (cm) | 1 | 4.49 | 3.16 |
| Stem Girth (cm) | 0.098 | 0.44 | 0.31 |
| Nodes main axis | 0.53 | 2.36 | 1.66 |
| Average Internode length (cm) | 0.085 | 0.38 | 0.27 |
| Number of main branches | 0.95 | 4.25 | 2.99 |
| Leaf stem ratio | 0.007 | 0.33 | 0.23 |
| Leaves on main axis | 0.88 | 3.94 | 2.77 |
| Leaf area ($cm^2$) | 0.11 | 0.48 | 0.34 |
| Herb Yield (T ha) | 0.38 | 1.71 | 1.2 |
| Oil Content (% V W) | 0.034 | 0.15 | 0.11 |
| Menthol (% V V) | 1.07 | 4.8 | 3.38 |
| Menthone | 0.84 | 3.78 | 2.66 |
| Neo-menthone | 0.32 | 1.45 | 1.02 |
| Menthyl acetate | 0.3 | 1.35 | 0.95 |
| Iso-menthone | 0.28 | 1.27 | 0.9 |
| Total oil yield (1 ha) | 1.24 | 5.57 | 3.92 |

SEM = Standard Error of Mean
CD (1%) = critical difference at 1% probability level
CD (5%) = critical difference at 5% probability level Thus, the new variety 'Pranjal' (CIMAP/MPP-4) is a selection from cloned population of *Mentha×piperita* and is characterized as a perennial, glabrous herb of 45–50 cm height having canopy 40–45 cm.

The following is an objective description of the new variety.

Genus: Mentha.
Species: *Piperita.*
Family: Lamiaceae.
Common name: Peppermint.
Plant height: About 50 cm.
Growth habit: Herb with slender creeping rootstocks sending up erect purple branches.
Stem: Red purple near (59A), quadrangular, girth about — 1.5 cm.
Leaf: Simple, Yellow green near (147A).
Texture: Soft Leather.
Surface: Rough due to sparse trichomes.
Shape: Ovate.
Margin: Serrated.
Tip: Acute.
Base: Tapering (Acute).
Size: Broad.
Length: About 5.5 cm.
Width: About 2.6 cm.
Petiole length: About 0.8 cm.
Area: About 5.8 $cm^2$.
Leaf-stem ratio: About 0.36.
Inflorescence:
*Form.*—Verticillaster.
*First flowering.*—Approximately the last week of July when transplanted in about the first week of February (165 days).
*Flower.*—Near purple white; diameter about 0.6 cm; mild fragrance.
*Pedicel.*—Color near 189A; length about 0.4 cm.
*Calyx.*—Near Yellow green (near 144A); diameter about 0.4 cm.
*Corolla.*—Near white (near 155C).
*Anthers.*—About four — near purple (near 184A) — rudimentary, remaining inside corolla tube.
*Stigma.*—Bifid, color near 155B.
*Ovary.*—Color near 138B.
Percent of oil content in fresh herb: About 0.8%.
Oil quality:
*Menthol content* (%).—About 51.59%.
*Menthone content*(%).—About 13.57%.
*Neo-menthone content* (%).—About 6.16%.
*Menthyl acetate* (%).—5.44%.
*Iso-menthone* (%).—3.08%.

RAPD profile (FIG. 3)

The flowers of 'Pranjal' do not set seed at Lucknow, India; accordingly, no dimensions are available. The plant has been reproduced asexually through suckers.

EVIDENCE OF UNIFORMITY AND STABILITY

The new variety (genotype CIMAP/MPP-4) has remained stable and uniform for its morphometric traits and showed consistent performance for oil yield and quality during its evaluation and multiplication in the years 1998 and 1999.

DELAYED TEMPORARY WILTING POINT

To assess the new variety for its hardiness an experiment was carried out to know the delayed temporary wilting point under controlled environmental conditions using both 'Pranjal' and control 'Kukrail'. Ten (10) cm long twigs (3 replications, 10 twigs each) were kept with their cut end dipped in sterile water in a test tube for 4 weeks at 30° C. The following table represents the percentage of wilting tabulated at the end of the month in the two genotypes ('Pranjal' and 'Kukrail') after 30 days:

| S1. No. | Genotype | Percentage of wilting |
|---|---|---|
| 1. | 'PRANJAL' | 3.3% |
| 2. | 'Kukrail' | 90.0% |

The new variety was tested for its tolerance to Bihar hairy caterpillar (*Spilarctia obliqua*). Studies on the plant in the years 1998, 1999 and 2000 revealed that the plant is highly tolerant to this infestation. The results are depicted here below:

| | Percentage of infestation in the year | | |
|---|---|---|---|
| Genotype | 1998 | 1999 | 2000 |
| 'PRANJAL' (CIMAP/MPP-4) | 9.9 | 8.3 | 8.6 |

-continued

| | Percentage of infestation in the year | | |
|---|---|---|---|
| Genotype | 1998 | 1999 | 2000 |
| 'Kukrail' | 45.5 | 56.3 | 64.3 |
| CD | 4.5 | 5.2 | 3.6 |

These values are based on observations recorded on 10 plants ach in three (3) replications over three (3) years.

Hence, 'Pranjal' has shown tolerance to this pest in comparison to 'Kukrail', the control plant.

SEQUENCE LISTING

```
<160> NUMBER OF SEQ ID NOS: 19

<210> SEQ ID NO 1
<211> LENGTH: 10
<212> TYPE: DNA
<213> ORGANISM: Artificial Sequence
<220> FEATURE:
<223> OTHER INFORMATION: Oligonucleotide primer for RAPD profile

<400> SEQUENCE: 1

aaatcggagc                                                          10


<210> SEQ ID NO 2
<211> LENGTH: 10
<212> TYPE: DNA
<213> ORGANISM: Artificial Sequence
<220> FEATURE:
<223> OTHER INFORMATION: Oligonucleotide primer for RAPD profile

<400> SEQUENCE: 2

gtcctactcg                                                          10


<210> SEQ ID NO 3
<211> LENGTH: 10
<212> TYPE: DNA
<213> ORGANISM: Artificial Sequence
<220> FEATURE:
<223> OTHER INFORMATION: Oligonucleotide primer for RAPD profile

<400> SEQUENCE: 3

gtccttagcg                                                          10


<210> SEQ ID NO 4
<211> LENGTH: 10
<212> TYPE: DNA
<213> ORGANISM: Artificial Sequence
<220> FEATURE:
<223> OTHER INFORMATION: Oligonucleotide primer for RAPD profile

<400> SEQUENCE: 4

tgcgcgatcg                                                          10


<210> SEQ ID NO 5
<211> LENGTH: 10
<212> TYPE: DNA
<213> ORGANISM: Artificial Sequence
<220> FEATURE:
```

-continued

<223> OTHER INFORMATION: Oligonucleotide primer for RAPD profile

<400> SEQUENCE: 5 aacgtacgcg 10

<210> SEQ ID NO 6
<211> LENGTH: 10
<212> TYPE: DNA
<213> ORGANISM: Artificial Sequence
<220> FEATURE:
<223> OTHER INFORMATION: Oligonucleotide primer for RAPD profile

<400> SEQUENCE: 6 gcacgccgga 10

<210> SEQ ID NO 7
<211> LENGTH: 10
<212> TYPE: DNA
<213> ORGANISM: Artificial Sequence
<220> FEATURE:
<223> OTHER INFORMATION: Oligonucleotide primer for RAPD profile

<400> SEQUENCE: 7 ctatcgccgc 10

<210> SEQ ID NO 8
<211> LENGTH: 10
<212> TYPE: DNA
<213> ORGANISM: Artificial Sequence
<220> FEATURE:
<223> OTHER INFORMATION: Oligonucleotide primer for RAPD profile

<400> SEQUENCE: 8 cgggatccgc 10

<210> SEQ ID NO 9
<211> LENGTH: 10
<212> TYPE: DNA
<213> ORGANISM: Artificial Sequence
<220> FEATURE:
<223> OTHER INFORMATION: Oligonucleotide primer for RAPD profile

<400> SEQUENCE: 9 gcgaattccg 10

<210> SEQ ID NO 10
<211> LENGTH: 10
<212> TYPE: DNA
<213> ORGANISM: Artificial Sequence
<220> FEATURE:
<223> OTHER INFORMATION: Oligonucleotide primer for RAPD profile

<400> SEQUENCE: 10 ccctgcaggc 10

<210> SEQ ID NO 11
<211> LENGTH: 10
<212> TYPE: DNA
<213> ORGANISM: Artificial Sequence
<220> FEATURE:
<223> OTHER INFORMATION: Oligonucleotide primer for RAPD profile

<400> SEQUENCE: 11 ccaagcttgc 10

-continued

<210> SEQ ID NO 12
<211> LENGTH: 10
<212> TYPE: DNA
<213> ORGANISM: Artificial Sequence
<220> FEATURE:
<223> OTHER INFORMATION: Oligonucleotide primer for RAPD profile

<400> SEQUENCE: 12 gtgcaatgag 10

<210> SEQ ID NO 13
<211> LENGTH: 10
<212> TYPE: DNA
<213> ORGANISM: Artificial Sequence
<220> FEATURE:
<223> OTHER INFORMATION: Oligonucleotide primer for RAPD profile

<400> SEQUENCE: 13 aggatacgtg 10

<210> SEQ ID NO 14
<211> LENGTH: 10
<212> TYPE: DNA
<213> ORGANISM: Artificial Sequence
<220> FEATURE:
<223> OTHER INFORMATION: Oligonucleotide primer for RAPD profile

<400> SEQUENCE: 14 aagatagcgg 10

<210> SEQ ID NO 15
<211> LENGTH: 10
<212> TYPE: DNA
<213> ORGANISM: Artificial Sequence
<220> FEATURE:
<223> OTHER INFORMATION: Oligonucleotide primer for RAPD profile

<400> SEQUENCE: 15 ggatctgaac 10

<210> SEQ ID NO 16
<211> LENGTH: 10
<212> TYPE: DNA
<213> ORGANISM: Artificial Sequence
<220> FEATURE:
<223> OTHER INFORMATION: Oligonucleotide primer for RAPD profile

<400> SEQUENCE: 16 ttgtctcagg 10

<210> SEQ ID NO 17
<211> LENGTH: 10
<212> TYPE: DNA
<213> ORGANISM: Artificial Sequence
<220> FEATURE:
<223> OTHER INFORMATION: Oligonucleotide primer for RAPD profile

<400> SEQUENCE: 17 catcccgaac 10

<210> SEQ ID NO 18
<211> LENGTH: 10
<212> TYPE: DNA
<213> ORGANISM: Artificial Sequence
<220> FEATURE:

-continued

```
<223> OTHER INFORMATION: Oligonucleotide primer for RAPD profile

<400> SEQUENCE: 18

ggactccacg                                                          10


<210> SEQ ID NO 19
<211> LENGTH: 10
<212> TYPE: DNA
<213> ORGANISM: Artificial Sequence
<220> FEATURE:
<223> OTHER INFORMATION: Oligonucleotide primer for RAPD profile

<400> SEQUENCE: 19

agcctgacgc                                                          10
```

We claim:

1. A new and distinct Peppermint plant named 'Pranjal' of the variety substantially as shown and described.

* * * * *